US00PP31595P2

(12) United States Plant Patent
Van Swieten

(10) Patent No.: US PP31,595 P2
(45) Date of Patent: Mar. 24, 2020

(54) ***PHALAENOPSIS* ORCHID PLANT NAMED 'PHALGIQUEJ'**

(50) Latin Name: ***Phalaenopsis* hybrid**
Varietal Denomination: PHALGIQUEJ

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,909

(22) Filed: Jul. 2, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 5/02; A01H 6/62
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALGIQUEJ', particularly characterized by having white, shaded, striped, dotted, and edged flowers with dark red-purple lips, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALGIQUEJ'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGIQUEJ'.

The new *Phalaenopsis* plant is a product of a planned breeding program conducted by the inventor in Bleiswijk, the Netherlands. The objective of this breeding program was to create a new *Phalaenopsis* plant with numerous attractive white, shaded, striped, dotted, and edged flowers with dark red-purple lips, suitable for potted plant production.

The new *Phalaenopsis* plant 'PHALGIQUEJ' is a result of cross-pollination made by the inventor in October 2009 in Bleiswijk, the Netherlands, of the proprietary female, or seed parent, *Phalaenopsis* hybrid '01-2093' (unpatented) with the proprietary male, or pollen parent, *Phalaenopsis* hybrid '4048-02' (unpatented).

The new *Phalaenopsis* was selected by the inventor as a single plant within the progeny of the stated cross-pollination in a controlled greenhouse in Bleiswijk, the Netherlands, in August 2012. Asexual reproduction of the new *Phalaenopsis* plant by meristem tissue culture since 2015 in Bleiswijk, the Netherlands, has demonstrated that the new variety reproduces true to type with all of the characteristics, as herein described, firmly fixed and retained through successive generations.

Plant Breeder's Rights for this variety have been applied for in the European Union on Sep. 25, 2018, by Applicant who obtained the subject matter disclosed directly from the Inventor. 'PHALGIQUEJ' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, the Netherlands, and can be used to distinguish 'PHALGIQUEJ' as a new and distinct variety of *Phalaenopsis* plant:

1) White, shaded, striped, dotted, and edged flowers with dark red-purple lips;
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2019. Colors in the photographs may differ from the color values cited in the detailed botanical description, which accurately describe the actual colors of the new variety.

DESCRIPTION OF THE NEW VARIETY

Figure 1:
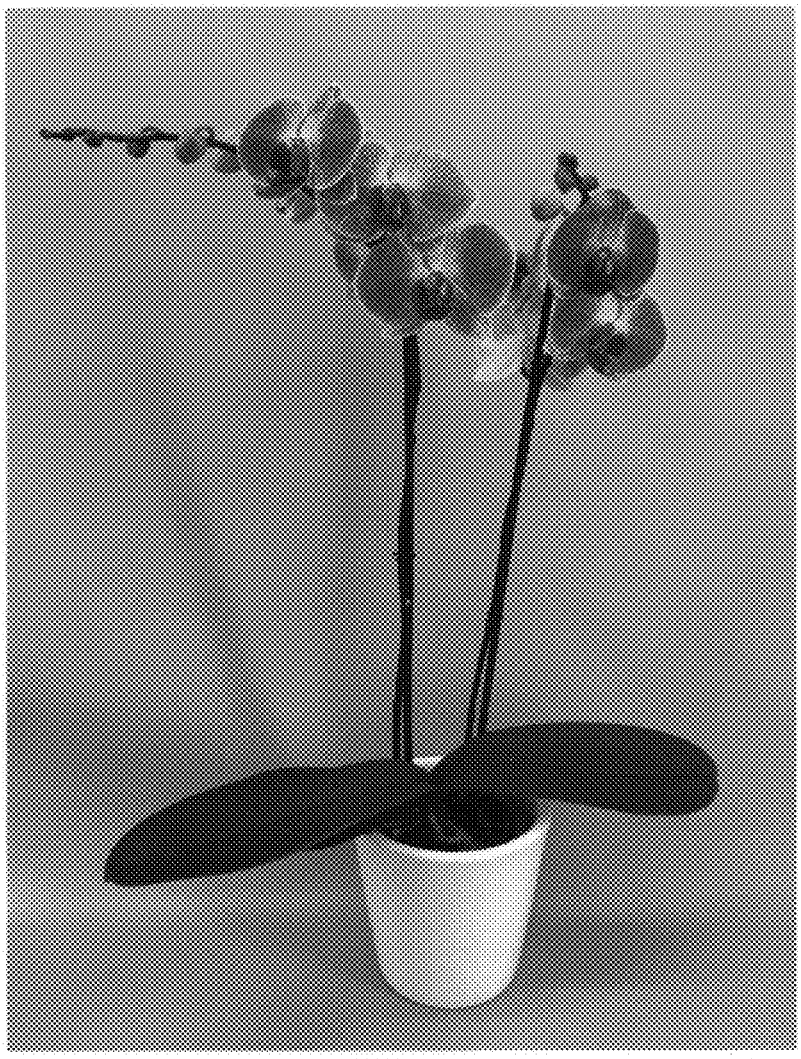
FIG. 1 shows the overall plant habit, including blooms, buds, and foliage of 'PHALGIQUEJ'.
Figure 2:
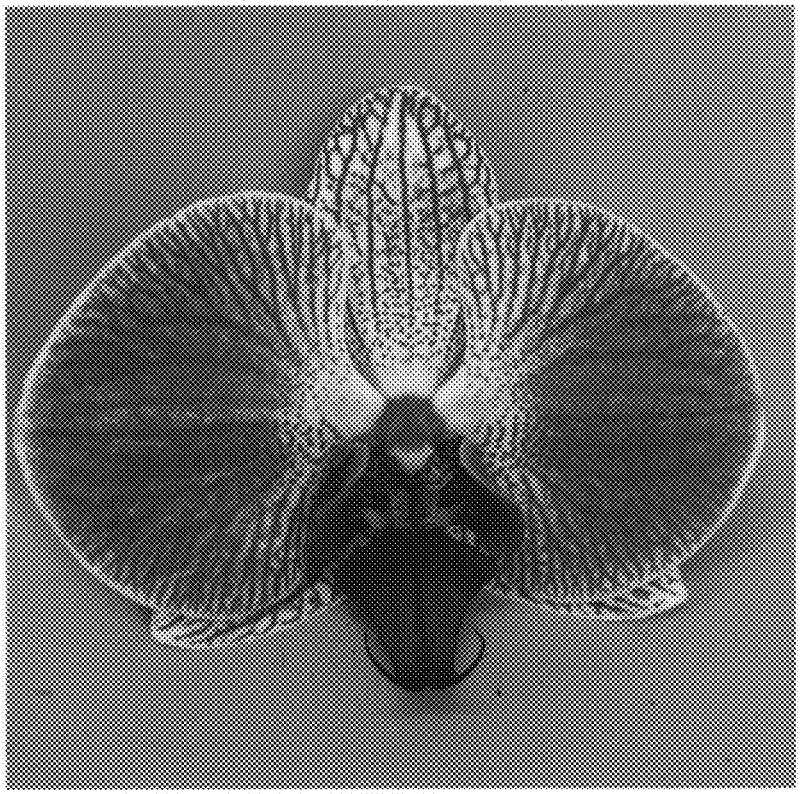
FIG. 2 shows a close-up of a flower of 'PHALGIQUEJ'.
Figure 3:
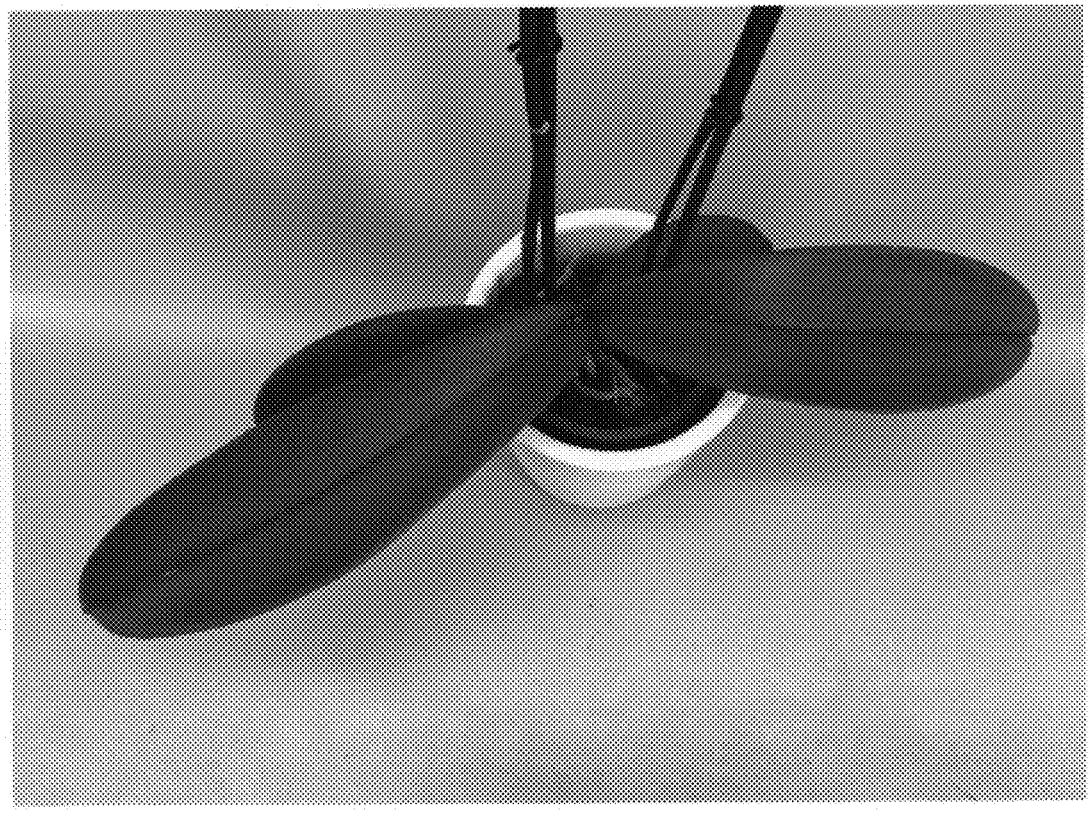
FIG. 3 shows an overhead view of the leaves of 'PHALGIQUEJ'.

The following detailed description sets forth the distinctive characteristics of 'PHALGIQUEJ'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGIQUEJ'.

Parentage:

*Female parent*.—*Phalaenopsis* cultivar '01-2093' (unpatented).

*Male parent*.—*Phalaenopsis* cultivar '4048-02' (unpatented).

Propagation:

*Type*.—Meristem tissue culture.

Roots:

*Root description*.—Greyed-green (between RHS 190B and 190C) colored roots with branching lateral roots having yellow-green (RHS 145A) colored root tips.

Plant:

*Commercial crop time to flowering*.—Following asexual propagation (in-vitro), the rooted cuttings grow for 20-24 weeks. After transplantation into 12-cm pots, the plants are finished after 48 to 50 weeks.

*Growth habit of peduncle*.—Upright to slightly pendant with raceme inflorescence.

*Height* (*from soil level to top of inflorescence*).—Approximately 53.0 cm to 63.0 cm.

*Width* (*measured from leaf tips*).—About 38.0 cm to 42.0 cm.

*Vigor*.—Strong.

Leaves:

*Mature leaves*.—Quantity per plant: 6 to 7 leaves are produced before flowering. Length (fully expanded): 21.0 cm to 24.0 cm. Width: 7.0 cm to 8.0 cm. Shape: Oblong. Base shape: Moderately elongated to very elongated. Apex: Obtuse unequal. Leaf blade angle with the petiole (measured from the horizontal position): Between 15 degrees and 25 degrees. Leaf margin: Entire. Color: Upper surface: RHS 146A. Lower surface: RHS 146B with a touch of diluting dark red (RHS 187A). Texture (both upper and lower surfaces): Rough. Thickness: 2.0 mm to 3.0 mm. Variegation: Absent. Venation: Pattern: Parallel. Color of the midvein: Upper surface: RHS 146A. Lower surface: Diluting dark red (RHS 187A).

Peduncle:

*Quantity per plant*.—1 to 3.

*Number of flowers per peduncle*.—9 to 13.

*Length*.—53.0 cm to 63.0 cm.

*Diameter*.—5.0 mm to 6.0 mm.

*Strength*.—Strong.

*Aspect*.—Upright to slightly pendant.

*Texture*.—Smooth.

*Color*.—Brown (RHS 200A) with a touch of green (RHS 146B).

*Internode length*.—3.0 cm to 4.0 cm.

Inflorescence description:

*Appearance*.—Upright to slightly pendant, raceme inflorescence with bilaterally symmetrical flowers that open in succession beginning with the lowermost flower.

*Number of inflorescences*.—1 to 3.

*Inflorescence size*.—Height (from base to tip): 230.0 mm to 260.0 mm.

*Flowering time*.—First flowers can be expected 10 to 11 months after planting in a 12-cm pot.

*Flower*.—Height: 77.0 mm to 82.0 mm. Diameter: 95.0 mm to 100.0 mm. Depth of lip: 26.0 mm to 28.0 mm.

*Flower longevity*.—On the plant: 14 to 19 weeks.

*Fragrance*.—Absent.

*Flower bud*.—Average size: Large. Length: 22.0 mm to 24.0 mm. Width: 19.0 mm to 21.0 mm. Shape: Egg shaped. Color: Light yellow-green (RHS 145B to 145C) with a touch of purplish-red (RHS N77B).

*Petals*.—Arrangement: Open/free. Shape: Semi-circular. Apex: Obtuse asymmetric. Margin: Entire. Length (from base to tip): 44.0 mm to 46.0 mm. Width: 55.0 mm to 57.0 mm. Position of the broadest part of the petal: Toward the base. Color (when fully opened): Upper surface: Basic color: White (RHS NN155C). Over color: Reddish-purple shade (RHS N78B); stripes and dots (RHS N78A). Lower surface: Basic color: White (RHS NN155C). Over color: Purplish-pink shade (RHS N78C) and diluting reddish-purple stripes (RHS N78B).

*Dorsal sepal*.—Shape: Elliptic. Apex: Obtuse symmetric. Margin: Entire. Length (from base to tip): 45.0 mm to 47.0 mm. Width: 30.0 mm to 32.0 mm. Color (when fully opened): Upper surface: Basic color: White (RHS NN155C). Over color: Reddish-purple dots at the base and stripes (RHS N78A); reddish-purple shade (RHS N78B). Lower surface: Basic color: White (RHS NN155C). Over color: Light yellow-green (RHS 145D) and diluting purplish-pink stripes (RHS N78C).

*Lateral sepals*.—Shape: Ovate. Apex: Obtuse asymmetric. Margin: Entire. Length (from base to tip): 43.0 mm to 45.0 mm. Width: 26.0 mm to 28.0 mm. Color (when fully opened): Upper surface: Basic color: White (RHS NN155C). Over color: Slightly light yellow-green (RHS 145D) with purplish-red dots (RHS 59B) at the base; striped (RHS N78A) and slightly shaded (RHS N78B). Lower surface: Basic color: White (RHS NN155C). Over color: Light yellow-green (RHS 145D) and diluting light reddish-purple stripes (RHS N78D).

*Labellum* (*lip*).—Whiskers: Present. Length of whiskers: 11.0 mm to 13.0 mm. Color of whiskers: Dark red-purple: at the base (RHS 187D) and toward the tip (RHS 187B). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated. Length: 21.0 mm to 23.0 mm. Width: 14.0 mm to 16.0 mm. Color: White (RHS NN155C) with dark red stripes (RHS 59A) at the base; purplish-red (RHS 59B) on one side; reddish-purple (RHS N78A to N78B) toward other side.

*Apical lobe*.—Shape: Triangular to ovate. Margin: Entire. Length: 22.0 mm to 24.0 mm. Width: 21.0 mm to 23.0 mm. Color: Dark red (RHS 59A to 59B) at the base and red-purple (mix of RHS NN78A and N79C) toward whiskers.

*Callus*.—Average size: Medium to large. Height: 7.0 mm to 8.0 mm. Length: 6.0 mm to 7.0 mm. Width: 4.0 mm to 5.0 mm. Color: Yellow (RHS 8A to 8B); dotted (RHS 183B).

Reproductive organs:

*Column*.—Length: 8.0 mm to 10.0 mm. Diameter: 5.0 mm to 6.0 mm. Color: Reddish-purple (RHS N78A).

*Pollinia*.—Quantity: 2. Diameter: 0.9 mm to 1.1 mm. Color: Orange (RHS 24A).

*Ovary*.—Length: 9.0 mm to 11.0 mm. Diameter: 2.4 mm to 2.8 mm. Color: Light yellow-green (RHS 147D) and very light purple (RHS 76C) toward the flower.

*Pedicel*.—Length: 38.0 mm to 40.0 mm. Diameter: 2.9 mm to 3.3 mm. Color: Yellow-green (RHS 147C) at the base; light yellow-green (RHS 147D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent of 'PHALGIQUEJ', cultivar '01-2093' (unpatented) is no longer in existence, therefore a meaningful comparison cannot be made.

'PHALGIQUEJ' differs from male parent plant '4048-02' (unpatented) in that 'PHALGIQUEJ' has obtuse petal apexes and obtuse dorsal sepal apexes, whereas '4048-02' has emarginated petal apexes and emarginated dorsal sepal apexes. Additionally, 'PHALGIQUEJ' has larger flowers than '4048-02'.

'PHALGIQUEJ' is most similar to the commercial *Phalaenopsis* plants named 'PHALFEWYP' (U.S. Plant patent application Ser. No. 16/501,156) and 'PHALVRABI' (unpatented). 'PHALGIQUEJ' differs from the commercial variety 'PHALFEWYP' in that 'PHALGIQUEJ' has obtuse dorsal sepal apexes and flowers with an upper surface basic color of white and having a shaded, dotted, and striped pattern, whereas 'PHALFEWYP' has emarginated dorsal sepal apexes and flowers with an upper surface basic color of reddish-purple and having a centered pattern.

'PHALGIQUEJ' differs from the commercial variety 'PHALVRABI' in that 'PHALGIQUEJ' has obtuse dorsal sepal apexes, whereas 'PHALVRABI' has slightly emarginated dorsal sepal apexes. Additionally, 'PHALGIQUEJ' has larger flowers than 'PHALVRABI'.

I claim:

1. A new and distinct variety of *Phalaenopsis* plant named 'PHALGIQUEJ', substantially as described and illustrated herein.

* * * * *